United States Patent [19]

Benson et al.

[11] 4,317,818

[45] Mar. 2, 1982

[54] METHOD OF TREATING PROSTATIC CARCINOMA

[75] Inventors: Harvey D. Benson, Cincinnati; Joyce F. Grunwell, Hamilton; John O. Johnston, Cincinnati, all of Ohio; Vladimir Petrow, Chapel Hill, N.C.

[73] Assignee: Richardson-Merrell Inc., Wilton, Conn.

[21] Appl. No.: 154,175

[22] Filed: May 28, 1980

Related U.S. Application Data

[63] Continuation of Ser. No. 32,828, Apr. 24, 1979, abandoned, which is a continuation of Ser. No. 841,892, Oct. 13, 1977, abandoned, which is a continuation-in-part of Ser. No. 684,946, May 10, 1976, abandoned.

[51] Int. Cl.³ .............................................. A61K 31/56
[52] U.S. Cl. ..................................................... 424/242
[58] Field of Search ........................................ 424/242

[56] References Cited

U.S. PATENT DOCUMENTS 3,235,573 2/1966 Bowers .............................. 260/397.4
3,449,381 6/1969 Bowers .............................. 260/397.4

Primary Examiner—Elbert L. Roberts
Attorney, Agent, or Firm—Millen & White

[57] ABSTRACT

Compounds of the following general formula are useful in treating prostatic carcinoma:

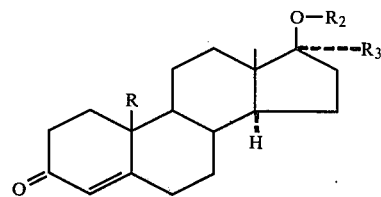

wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17-position carbon atom and the oxygen atom.

6 Claims, No Drawings

METHOD OF TREATING PROSTATIC CARCINOMA

This is a continuation of application Ser. No. 032,828, filed Apr. 24, 1979, which is in turn a continuation of Ser. No. 841,892, filed Oct. 13, 1977, which is a continuation-in-part of Ser. No. 684,946, filed May 10, 1976, all now abandoned.

FIELD OF INVENTION

This invention relates to methods of treating prostatic carcinoma and pharmaceutical compositions useful for said treatment.

BACKGROUND OF INVENTION

Adenocarcinoma of the prostate accounts for the greatest number of malignancies in men over 65. Early and localized prostatic carcinoma is often treated by removal of the prostate. Surgical cure may not be possible when metastases is extensive requiring in addition to surgical treatment hormonal therapy. Estrogens, for example, diethylstilbestrol and corticosteroids, for example, cortisone, have been used in the control of prostatic carcinoma. Although estrogen treatment has been reported to often result in improvement of the condition certain undesirable side effects also occur. For example, it is known that prolonged administration of estogens to males can result in the occurrence of gynecomastia and impotence. Also, estrogens are known to interfere with blood clotting mechanisms resulting in thrombosis and stroke. The method provided by the present invention avoids the undesirable side effects associated with estrogen therapy.

Some of the compounds employed in this invention, for example, 19-hydroxyandrost-4-ene-3,17-dione and the 19-oxo-derivative thereof have been involved in numerous in vitro studies wherein the role of the metabolism of androgens has been investigated. Additionally, 19-hydroxyandrost-4-ene-3,17-dione is reported to have been administered to two healthy male subjects each 21 years of age (J. Clin. Endocrinol. Metab. 28 1401 (1968)). Also, 3-oxo-17β-hydroxy-androst-4-ene-19-al has been reported in U.S. Pat. No. 3,235,573 issued Feb. 15, 1966, and U.S. Pat. No. 3,449,381 issued June 10, 1969, wherein the utilities disclosed are anabolic-androgenic activity, inhibition of pituitary gonadotrophins and adrenocorticotrophin, anti-estrogenic, blood, liver and adrenal cholesterol lowering properties, control of fertility and psychotic conditions, and appetite stimulants. To applicants' knowledge the use of the compounds employed in the present invention in the treatment of prostatic carcinoma has not been taught or suggested heretofore.

SUMMARY OF INVENTION

This invention relates to a method of treating prostatic carcinoma by administering a compound of the following general formula:

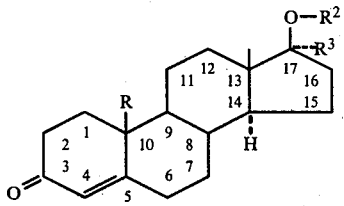

Formula I wherein R is —CHO or —CH$_2$OR$_1$; each of R$_1$ and R$_2$ is hydrogen, alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms; R$_3$ is hydrogen; or R$_2$ and R$_3$ together form a double bond between the 17-position carbon atom and the oxygen atom.

DETAILED DESCRIPTION OF INVENTION

In the compounds of general Formula I the term alkylcarbonyl is taken to mean a group of the structure alkyl

wherein the alkyl moiety has from 1 to 20 carbon atoms and is a straight chain or a branched chain. Illustrative examples of the alkyl moiety in the substituent alkylcarbonyl group are methyl, ethyl, n-propyl, isopropyl, n-butyl, sec-butyl, tert-butyl, n-pentyl, neopentyl, pivalyl, hexyl, heptyl, octyl, 2,4-dimethyloctyl, undecyl, 9-methylundecyl, pentadecyl, hexadecyl, dodecyl, 2,4,6-trimethyldecyl, heptadecyl, decyl, octadecyl, nonadecyl and didecyl.

The term benzoyl as used in reference to the compounds of general Formula I is taken to mean the group

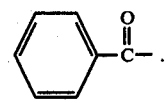

The term phenylalkylcarbonyl as used in reference to the compounds of general Formula I is taken to mean a substituent group of the structure

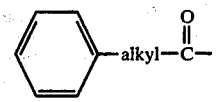

wherein the alkyl moiety, which may also be referred to as an alkylene moiety, has from 1 to 6 carbon atoms and is a straight chain or a branched chain. Illustrative examples of the alkyl moiety in the substituent phenylalkylcarbonyl group are methyl, ethyl, n-propyl, n-butyl, n-pentyl, hexyl, isopropyl, sec-butyl, tert-butyl and neopentyl.

Illustrative example of cycloalkylcarbonyl groups which R$_1$ and R$_2$ may be are cyclopentanecarbonyl, cyclohexanecarbonyl, cyclooctanecarbonyl, 1- or 2-norbornanecarbonyl and 1- or 2-adamantanecarbonyl.

It is apparent from the foregoing general Formula I that the compounds employed in the instant invention are androst-4-ene-3,17-diones having a —CH$_2$OR$_1$ or —CHO group at the 10β-position as represented respectively by the following general Formulas II and III, or are 17β-hydroxyandrost-4-en-3-one derivatives or esters thereof as defined by R$_2$ having a —CH$_2$OR$_1$ or —CHO group present at the 10β-position as represented respectively by the following general Formulas IV and V:

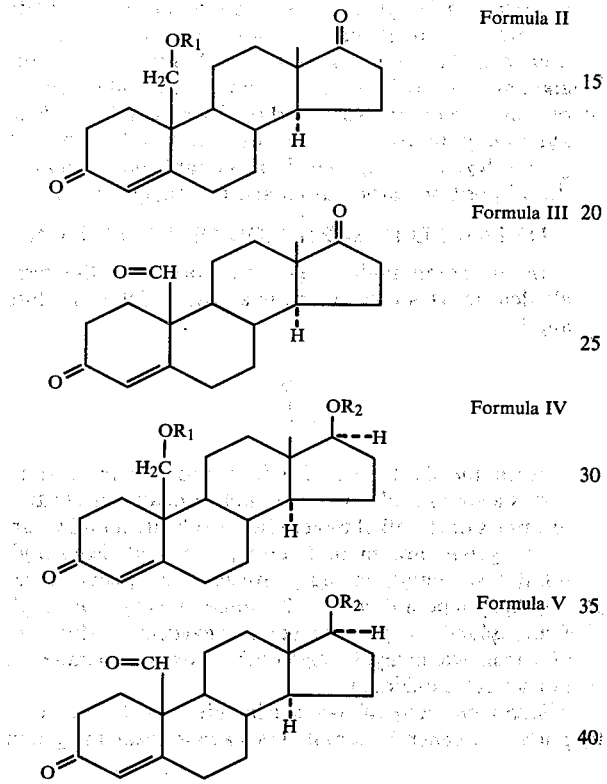

Formula II

Formula III

Formula IV

Formula V

In general Formulas II and IV R$_1$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or cycloalkylcarbonyl wherein the cycloalkyl moiety has from 5 to 10 carbon atoms as defined hereinabove.

In general Formulas IV and V the hydrogen atom attached to the 17-position is in the alpha position, and R$_2$ is hydrogen or alkylcarbonyl wherein the alkyl moiety has from 1 to 20 carbon atoms and is straight or branched, benzoyl, phenylalkylcarbonyl wherein the alkyl moiety has from 1 to 6 carbon atoms and is straight or branched or, cycloalkyl-carbonyl wherein the cycloalkyl moiety has from 5 to 10 carbon atoms as defined hereinabove.

The use of the compounds as represented by each of general Formula II and III in the treatment of prostatic carcinoma represents a more specifically preferred embodiment of this invention. Other embodiments of this invention are the use of the compounds as represented by general Formulas IV and V in the treatment of prostatic carcinoma with the use of the compounds of general Formula IV wherein R$_1$ and R$_2$ each represent hydrogen and the compounds of general Formula V wherein R$_2$ represents hydrogen being more preferred embodiments.

Illustrative examples of compounds employed in the present invention are 17β,19-bis(1-oxopropoxy)androst-4-en-3-one, 17β,19-bis(1-oxodidecyloxy)androst-4-en-3-one, 17β,19-dihydroxyandrost-4-en-3-one, 19-hydroxy-17β-(1-oxopropoxy)-androst-4-en-3-one, 19-hydroxy-17β-(1-oxohexadecyloxy)androst-4-en-3-one, 19-acetoxyandrost-4-ene-3,17-dione, 19-acetoxy-17β-hydroxyandrost-4-en-3-one, 3-oxo-17β-hydroxyandrost-4-en-19-al, 19-(1-adamantanylcarbonyloxy)androst-4-ene-3,17-dione, 19-(1-norbornylcarbonyloxy)androst-4-ene-3,17-dione, 19-(1-cyclopentylcarbonyloxy)androst-4-ene-3,17-dione, 3,17-dioxoandrost-4-en-19-al and 3-oxo-17β-(1adamantanylcarbonyloxy)androst-4-en-19-al.

The compounds employed in the present invention can be administered to a patient in need thereof in various manners to achieve the desired effect. The compounds can be administered alone or in the form of pharmaceutical preparations to the patient being treated either orally or parenterally, that is, subcutaneously and intramuscularly including injection of the active ingredient directly into the prostate. The amount of compound administered can vary over a wide range to achieve the desired effect and will vary with the mode of administration. For example, smaller dosages may be required when the active ingredient is injected directly into the prostate than when the active ingredient is administered orally. The amount of compound administered can vary from about 0.1 to about 500 mg/kg and preferably from about 0.1 to 250 mg/kg. These dosage ranges represent the amount of compound that will be effective in treating prostatic carcinoma. For parenteral administration and particularly for injection of the active ingredient directly into the prostate gland a lesser dose, for example, from 0.1 to 25 mg/kg may be used.

As used herein the term patient is taken to mean a warm blooded male mammal, such as dogs, or rodents having prostatic carcinoma.

For oral administration the compounds can be formulated into solid or liquid preparation such as capsules, pills, tablets, troches, powders, solutions, suspensions or emulsions. The solid unit dosage forms can be of the conventional type. Thus, the solid form can be a capsule which can be of the ordinary gelatin type containing a compound of general Formula I and a carrier, for example, lubricants and inert filler such as lactose, sucrose and cornstarch. In another embodiment the compounds of general Formula I can be tableted with conventional tablet bases such as lactose, sucrose and cornstarch in combination with binders such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds employed in the present invention, that is, the compounds of general Formula I can be used in combination with surgical removal of the prostate.

Following are illustrative pharmaceutical formulations which may be employed in practicing the present invention:

| Tablet | For 15,000 |
|---|---|
| 3,17-Dioxoandrost-4-en-19-al Fine Powder | 2.625 kg |
| Lactose | 6.750 kg |
| Corn Starch | 0.563 kg |

Mix the active ingredient, the lactose and cornstarch uniformly. Granulate with 10% starch paste. Dry to a moisture content of about 2.5%. Screen through a No. 12 mesh screen. Add and mix the following:

| Magnesium Stearate | 0.225 kg |
|---|---|
| Corn Starch qs ad | 11.250 kg |

Compress on a suitable tablet machine to a weight of 0.750 g/tablet.

| Soft Gelatin Capsule | |
|---|---|
| 3,17-Dioxoandrost-4-en-19-al | 0.25 kg |
| Polysorbate 80 | 0.25 kg |
| Corn Oil qs ad | 25.0 kg |

Mix and fill into 50,000 soft gelatin capsules.

| IM Depot Injection | |
|---|---|
| Each 1 ml contains the following: | |
| 3,17-Dioxoandrost-4-en-19-al | 5.0 mg |
| Anhydrous Chlorobutanol | 5.0 mg |
| Aluminum Monostearate | 50.0 mg |
| Peanut Oil qs ad | 1.0 ml |

Dissolve or disperse the ingredients in the peanut oil.

| Depot - Implant | |
|---|---|
| 3,17-Dioxoandrost-4-en-19-al micronized | 5 mg |
| Dimethylsilioxane | 240 mg |
| Catalyst qs | |

Disperse the drug substance in the fluid dimethylsiloxane. Add the catalyst and cast into a suitable monolytic structure. Alternatively, the drug substance may be enclosed by a pre-cast polydimethylsiloxane envelope. Alternatively, the drug substance may be dispersed in a suitable amount of hydroxyethyl acrylate subsequently polymerized and cross-linked by the addition of ethylenedimethacrylate, and an oxidizing agent, to yield a 3-dimensional ethylene glycomethacrylate mouldable gel (Hydron).

| Injections | |
|---|---|
| A. Oil Type: | |
| 3,17-Dioxoandrost-4-en-19-al | 25 mg |
| BHA, BHT (of each) | 0.01% w/v |
| Peanut Oil or Sesame Oil qs | 1.0 ml |
| B. Suspension Type: | |
| 3,17-Dioxoandrost-4-en-19-al | 25 mg |
| Sodium Carboxymethyl cellulose | 0.5% w/v |
| Sodium Bisulfite | 0.02% w/v |
| Water for injection, qs | 1.0 ml |

| Buccal or Sublinqual Tablet | |
|---|---|
| 3,17-Dioxoandrost-4-en-19-al | 1% |
| Calcium Stearate | 1% |
| Calcium Saccharin | 0.02% |
| Granular Mannitol | qs |

Mix and compress on a suitable tablet maching to a weight of 0.115 g/tablet.

Administration of the compounds of general Formulas I to V to a patient in need thereof in the effective amounts described hereinabove provides an effective method of treating or controlling prostatic carcinoma without the occurrence of certain deleterious side effects known to occur with the administration of estrogenic agents including thrombotic effects, such as blood clotting and feminizing effects such as gynecomastia and male impotence. Administration of the compounds employed in the present invention in amounts higher than the amount specified above as an effective amount may result in these deleterious estrogenic side effects.

It has been found that the compounds employed in the present invention have a markedly reduced thrombotic potential as compared to estrogen. For example, 3,17-dioxoandrost-4-en-19-al was given subcutaneously to ovariectomized albino rats for seven days at either 0.1 or 3.0 mg/kg. Body weight and uterine weights were measured. Blood samples were taken and the effect of thrombotic potential determined through measurements of anti-thrombin III activity, ethanol gel tests, (fibrin monomer level), protamine sulfate test (fibrin degradation product), adenosinephosphate and collagen induced platelet aggregation. Anti-thrombin activity was not affected nor was increased fibrin monomer or fibrin degradation product level detected. Platelet aggregation was not significantly changed.

The utility of the compounds employed in the present invention in the treatment of prostatic carcinoma can be demonstrated in the Dunning R3327H rat prostatic adenocarcinoma model which is recognized in the art as fulfilling the criteria for an animal model of carcinoma of the prostate (J. K. Smolev et al., Cancer Treatment Reports 61, No. 2, 273–287 (1977). Representative compounds employed in the present invention have been shown to significantly reduce the growth rate of the R3327H adenocarcinoma over a 70 day period at a dose of 0.3 mg/kg/day. Additionally, representative compounds employed in the present invention decrease prostate weight, decrease 5α reductase activity, and produce no significant changes in the weight of test animals (rats) thus fulfilling three additional criteria recognized in the art as being characteristic of an anti-prostatic carcinoma agent (Normal and Abnormal Growth of the Prostate, ed. M. Goland, Springfield, Ill., Charles C. Thomas, 1975, pp. 754-5).

Many of the compounds employed in the present invention are known in the art or are commercially available. For example, 19-hydroxyandrost-4-ene-3,17-dione, 17β,19-dihydroxyandrost-4-en-3-one, 19-hydroxy-17β-(1-oxoethoxy)androst-4-en-3-one, 19-hydroxy-17β-(1-oxobenzyloxy)androst-4-en-3-one, and 3-oxo-17β-(1-oxobenzyloxy)androst-4-en-19-al are commercially available.

The esters of the compounds employed in the present invention, that is, compounds wherein either or both of $R_1$ and $R_2$ are alkylcarbonyl wherein the alkyl moiety has from 1 to 20 carbon atoms and is straight or branched, cycloalkylcarbonyl wherein the cycloalkyl moiety has from 5 to 10 carbon atoms, benzoyl and phenylalkylcarbonyl wherein the alkyl moiety has from 1 to 6 carbon atoms and is straight or branched can be prepared as follows although other methods may also be employed. Ester derivatives of 19-hydroxyandrost-4-ene-3,17-dione and bis-ester derivatives of 17β,19-dihydroxyandrost-4-en-3-one are prepared by reacting the corresponding 19-hydroxy or 17β,19-dihydroxy compound with an appropriate acid anhydride of the formula

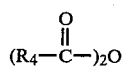

or acid chloride of the formula

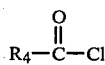

wherein $R_4$ is an alkyl group of from 1 to 20 carbon atoms and is straight or branched, a cycloalkyl group of from 5 to 10 carbon atoms, phenyl or phenylalkyl wherein the alkyl moiety has from 1 to 6 carbon atoms and is straight or branched in the presence of a base such as pyridine, quinoline or trialkylamine, such as, triethylamine, which base serves as the solvent, or from 1 to 24 hours at a temperature of from about 25° C. to 100° C. The appropriate acid anhydride or acid chloride are known in the art or can be prepared from the corresponding acids by procedures well known in the art.

Compounds employed in the present invention wherein $R_1$ is hydrogen and $R_2$ forms an ester group are prepared from the above obtained 17β,19-diester derivatives by refluxing the diester with one equivalent of sodium bicarbonate or potassium bicarbonate or one-half equivalent of sodium carbonate or potassium carbonate or dilute sodium hydroxide or potassium hydroxide solution in a lower alcohol solvent such as methanol or ethanol and water for about one hour, the reflux temperature depending on the solvent system employed.

Compounds employed in the present invention wherein R is CHO and $R_2$ forms an ester group are prepared by dissolving the above obtained compounds wherein $R_1$ is hydrogen and $R_2$ forms an ester group in acetone cooled to 0° to 10° C. and treating the solution with sufficient Jones reagent to effect the oxidation. Jones reagent is prepared by standard procedures using 26.72 grams of chromium trioxide, 23 ml of concentrated sulfuric acid and water to make 100 ml. The Jones reagent can be added to the solution until the reddish brown color persists which requires about 289 ml. Other oxidizing agents can be used, such as, dicyclohexylcarbodiimide in dimethylsulfoxide.

The following specific examples further illustrate the preparation of compounds employed in the instant invention.

EXAMPLE 1

17β,19-Bis(1-oxopropoxy)androst-4-en-3-one

A solution of 10 g of 17β,19-dihydroxyandrost-4-en-3-one which is commercially available and 25 ml of propionic anhydride in 200 ml of pyridine is allowed to stand overnight after which 100 ml of ethanol is added, and the reaction mixture is stirred for one hour. The mixture is then poured into one liter of water and the solid product is collected by filtration. The solid is dissolved in ether, dried over magnesium sulfate, filtered and the solvent removed. The residue is dissolved in hot hexane and allowed to cool yielding 17β,19-bis(1-oxopropoxy)-androst-4-en-3-one. M.P. 82°-84° C.

EXAMPLE 2

17β,19-Dihydroxyandrost-4-en-3-one

A solution of 150 g of 19-hydroxyandrost-4-en-3-one in 6 liters of ethanol is cooled in an ice bath. To this cold solution is added 13.5 g of potassium borohydride, and the reaction mixture is stirred for two hours at about 0° C. after which a second 13.5 g or potassium borohydride is added. Two hours later a third 13.5 g portion of potassium borohydride is added to the reaction mixture which is stirred for an additional one hour then poured into 11 liters of water to which 70 ml of acetic acid is added. The ethanol is distilled off under reduced pressure and the aqueous residue cooled to 0° C. The solid which separates is filtered off, dried and dissolved in 25 liters of hot chloroform after which the temperature is adjusted to 25° C. To the chloroform solution is added 250 g of manganese dioxide, and the mixture is stirred for two hours then filtered and the solvents removed under reduced pressure. The solid residue is recrystallized from acetonitrile to give 17β,19-dihydroxyandrost-4-en-3-one. M.P. 205°-207° C.

EXAMPLE 3

19-Hydroxy-17β-(1-oxopropoxy)androst-4-en-3-one

A solution of 11 g of 17β,19-bis(1-oxopropoxy)androst-4-en-3-one in 2 liters of methanol is treated with 2.5 g of sodium carbonate in 250 ml of water and refluxed for one hour after which the reaction mixture is poured into 10 liters of water, and the solid collected by filtration. The solid is dissolved in methylene chloride, dried over magnesium sulfate, filtered and the solvent removed. The residue is crystallized from acetone-hexane yielding 6 g of 19-hydroxy-17β(1-oxopropoxy)androst-4-en-3-one. M.P. 160°-162° C.

EXAMPLE 4

19-Acetoxyandrost-4-ene-3,17-dione

A solution of 19-hydroxyandrost-4-ene-3,17-dione in acetic anhydride and pyridine is allowed to stand overnight after which the reaction mixture is poured into ice water. The resulting solid is collected, dried and recrystallized from hexane to give 19-acetoxyandrost-4-ene-3,17-dione.

EXAMPLE 5

19-Acetoxy-17β-hydroxyandrost-4-en-3-one

To a solution of 25.6 g of 19-acetoxyandrost-4-ene-3,17-dione in 4 liters of methanol cooled to 0° C. is added 3.1 g of sodium borohydride, and the mixture is stirred at 0° C. for one hour after which 30 ml of acetic acid is added and the methanol removed under reduced pressure. The resulting residue is taken up in ethyl acetate and washed with water. The organic layer is dried over magnesium sulfate, filtered and the solvent removed. The solid residue is dissolved in 2 liters of chloroform treated with 125 g of manganese dioxide and stirred for two hours. The reaction mixture is filtered, and the solvent removed under reduced pressure. The residue is chromatographed on alumina using benzene-ether (1:1) as the eluant. The product is recrystallized from acetone-hexane to give 19-acetoxy-17β-hydroxyandrost-4-en-3-one, M.P. 125°–127° C.

EXAMPLE 6

19-Hydroxy-17β-(2'-tetrahydropyranyloxy)androst-4-en-3-one

To a solution of 10 g of 19-acetoxy-17β-hydroxyandrost-4-en-3-one in 300 ml of dihydropyran is added a small crystal of p-toluene sulfonic acid. The reaction mixture is allowed to stand overnight after which it is dissolved in ether and extracted with dilute sodium bicarbonate. The ether layer is dried over magnesium sulfate, filtered and the solvent removed. The resulting residue is dissolved in 2 liters of methanol and 2.5 g of sodium bicarbonate in 250 ml of water is added. The methanol solution is refluxed for one hour after which the solvent is removed under reduced pressure at 40° C. The residue is covered with water, and the solid crude product collected and re-crystallized from ethylacetate yielding 19-hydroxy-17β-(2'-tetrahydropyranyloxy)androst-4-en-3-one. M.P. 193°–199° C.

EXAMPLE 7

3-Oxo-17β-hydroxyandrost-4-en-19-al

A solution of 7 g of 19-hydroxy-17β-(2'-tetrahydropyranyloxy)androst-4-en-3-one in 500 ml of acetone is cooled to 10° C. and 5.3 ml of Jones reagent is added drop-wise. The reaction is stirred for an additional ten minutes then poured into water and extracted with ethylacetate. The ethylacetate extract is dried over magnesium sulfate, filtered and the solvent removed under reduced pressure. The residue is dissolved in 250 ml of 95% ethanol and 2 ml of concentrated hydrochloridic acid is added. The ethanol solution is refluxed for one hour then cooled to room temperature and neutralized with solid sodium carbonate. The neutralized solution is diluted with water and extracted with ethyl acetate. The extract is dried over magnesium sulfate, filtered and the solvent removed leaving a residue which is chromatographed on alumina using 25% ether in benzene as the eluant to give the product 3-oxo-17β-hydroxyandrost-4-en-19-al, M.P. 125°–127° C.

EXAMPLE 8

19-(1-Adamantanylcarbonyloxy)androst-4-ene-3,17-dione

A solution of 22 g of 19-hydroxyandrost-4-ene-3,17-dione, 18 g of 1-adamantanecarboxylic acid chloride, and 29 ml of pyridine in 2.2 liters of toluene is refluxed overnight. The reaction mixture is cooled, and the toluene layer is washed with water, dried over magnesium sulfate and filtered then the solvent is removed. The resulting residue is crystallized from methanol to give 19-(1-adamantanylcarbonyloxy)androst-4-ene-3,17-dione, M.P. 161°–163° C.

EXAMPLE 9

3,17-Dioxoandrost-4-en-19-al

To a solution of 30 g of 19-hydroxyandrost-4-ene-3,17-dione in 3 liters of acetone cooled in an ice bath is added 28 ml of Jones reagent over a one hour period. The reaction mixture is stirred for an additional fifteen minutes, filtered and the solvent removed under reduced pressure at 35° C. The residue is taken up in a large volume of ether and 1.5 liters of water. The ether layer is collected, dried over magnesium sulfate, filtered and the solvent removed. The residue is crystallized from acetone-hexane to give 3,17-dioxoandrost-4-en-19-al, M.P. 126°–129° C.

EXAMPLE 10

3-Oxo-17β-(1-oxopropoxy)androst-4-en-19-al

To a solution of 14 g of 19-hydroxy-17β-(1-oxopropoxy)androst-4-en-3-one in 1 liter of acetone cooled in an ice bath is added 13.3 ml of Jones reagent over one hour after which the reaction mixture is poured into a large volume of water and extracted with ether. The ether extract is dried over magnesium sulfate, filtered and the solvent removed. The residue is crystallized from acetone-hexane to give 3-oxo-17β(1-oxopropoxy)-androst-4-en-19-al, M.P. 119°–121° C.

We claim:

1. A method of reducing the growth rate of prostatic carcinoma in a patient in need thereof which comprises administering to said patient an effective amount of 3,17-dioxoandrost-4-en-19-al.
2. The method of claim 1 wherein the compound is administered in an amount of from 0.1 to 500 mg/kg.
3. The method of claim 2 wherein the compound is administered orally.
4. The method of claim 1 wherein the compound is administered in an amount of from 0.1 to 250 mg/kg.
5. The method of claim 4 wherein the compound is administered orally.
6. The method of claim 4 wherein the compound is administered parenterally.

* * * * *